US008768487B2

(12) United States Patent
Farnan et al.

(10) Patent No.: US 8,768,487 B2
(45) Date of Patent: Jul. 1, 2014

(54) DEVICES, METHODS AND SYSTEMS FOR ESTABLISHING SUPPLEMENTAL BLOOD FLOW IN THE CIRCULATORY SYSTEM

(75) Inventors: Robert C. Farnan, Rivervale, NJ (US); Oliver Marseille, Aachen (DE); Wolfgang Kerkhoffs, Aachen (DE)

(73) Assignee: Circulite, Inc., Teaneck, NJ (US)

( * ) Notice: Subject to any disclaimer, the term of this patent is extended or adjusted under 35 U.S.C. 154(b) by 298 days.

(21) Appl. No.: 13/025,757

(22) Filed: Feb. 11, 2011

(65) Prior Publication Data

US 2011/0196190 A1    Aug. 11, 2011

Related U.S. Application Data

(60) Provisional application No. 61/303,351, filed on Feb. 11, 2010.

(51) Int. Cl.
  *A61N 1/36* (2006.01)
  *A61M 1/12* (2006.01)
  *A61M 1/36* (2006.01)
  *A61B 17/00* (2006.01)

(52) U.S. Cl.
  CPC .............. *A61M 1/3653* (2013.01); *A61M 1/122* (2014.01); *A61B 2017/00252* (2013.01); *A61M 1/3659* (2014.01); *A61F 2210/0076* (2013.01)
  USPC ....................................................... 607/116

(58) Field of Classification Search
  USPC ....................................................... 607/116
  See application file for complete search history.

(56) References Cited

U.S. PATENT DOCUMENTS

| 3,903,895 | A | 9/1975 | Alley et al. |
| 4,033,331 | A | 7/1977 | Guss et al. |
| 4,790,825 | A | 12/1988 | Bernstein et al. |
| 5,190,528 | A | 3/1993 | Fonger et al. |
| 5,443,497 | A | 8/1995 | Venbrux |
| 5,456,712 | A | 10/1995 | Maginot |
| 5,676,670 | A | 10/1997 | Kim |
| 5,738,649 | A | 4/1998 | Macoviak |

(Continued)

FOREIGN PATENT DOCUMENTS

| WO | 99/59652 A1 | 11/1999 |
| WO | 2005/037345 A2 | 4/2005 |

OTHER PUBLICATIONS

United States Patent and Trademark Office, "Non-final Office Action," in related U.S. Appl. No. 13/204,201 mailed on May 9, 2012, 11 pp.

(Continued)

*Primary Examiner* — Amanda Patton
(74) *Attorney, Agent, or Firm* — Wood, Herron & Evans, L.L.P.

(57) ABSTRACT

A cannula for insertion through a biologic tissue. The cannula includes a shaft having proximal and distal end portions with a lumen therebetween. The cannula further includes a tip having a proximal end portion, a distal tip end, and a lumen therebetween. The proximal end portion of the tip is secured to the distal end portion of the shaft so that the lumen of the tip is in fluid communication with the lumen of the shaft. The tip includes an opening that extends proximally relative to the distal tip end to permit the flow of fluid into the lumen of the tip even in the event that the distal tip end becomes obstructed.

33 Claims, 14 Drawing Sheets

(56) References Cited

U.S. PATENT DOCUMENTS

| | | | |
|---|---|---|---|
| 5,797,960 A | 8/1998 | Stevens et al. | |
| 5,858,009 A | 1/1999 | Jonkman | |
| 5,944,745 A | 8/1999 | Rueter | |
| 5,947,940 A | 9/1999 | Beisel | |
| 5,961,545 A | 10/1999 | Lentz et al. | |
| 5,965,089 A | 10/1999 | Jarvik et al. | |
| 6,019,788 A | 2/2000 | Butters et al. | |
| 6,176,848 B1 | 1/2001 | Rau et al. | |
| 6,186,999 B1 | 2/2001 | Chen | |
| 6,217,546 B1 | 4/2001 | Hinchliffe et al. | |
| 6,299,575 B1 | 10/2001 | Bolling | |
| 6,358,532 B2 | 3/2002 | Starling et al. | |
| 6,475,232 B1 | 11/2002 | Babbs et al. | |
| 6,524,334 B1 | 2/2003 | Thompson | |
| 6,558,414 B2 | 5/2003 | Layne | |
| 6,565,536 B1 | 5/2003 | Sohn | |
| 6,579,314 B1 | 6/2003 | Lombardi et al. | |
| 6,652,544 B2 | 11/2003 | Houser et al. | |
| 6,740,115 B2 | 5/2004 | Lombardi et al. | |
| 6,770,087 B2 | 8/2004 | Layne et al. | |
| 6,786,920 B2 | 9/2004 | Shannon et al. | |
| 6,790,225 B1 | 9/2004 | Shannon et al. | |
| 6,808,533 B1 | 10/2004 | Goodwin et al. | |
| 6,866,805 B2 | 3/2005 | Hong et al. | |
| 6,911,040 B2 | 6/2005 | Johnson et al. | |
| 6,926,662 B1 | 8/2005 | Aboul-Hosn et al. | |
| 6,946,173 B2 | 9/2005 | Lim et al. | |
| 6,955,175 B2 | 10/2005 | Stevens et al. | |
| 6,984,243 B2 | 1/2006 | Dwyer et al. | |
| 6,989,071 B2 | 1/2006 | Kocur et al. | |
| 6,994,666 B2 | 2/2006 | Shannon et al. | |
| 7,077,801 B2 | 7/2006 | Haverich | |
| 7,083,640 B2 | 8/2006 | Lombardi et al. | |
| 7,108,717 B2 | 9/2006 | Freidberg | |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,780,692 B2 | 8/2010 | Nance et al. | |
| 2002/0169495 A1 | 11/2002 | Gifford et al. | |
| 2003/0125790 A1 | 7/2003 | Fastovsky et al. | |
| 2003/0195535 A1 | 10/2003 | Swanson et al. | |
| 2004/0015150 A1 | 1/2004 | Zadno-Azizi | |
| 2004/0182511 A1 | 9/2004 | Rakos et al. | |
| 2005/0065594 A1 | 3/2005 | DiMatteo et al. | |
| 2005/0124937 A1 | 6/2005 | Kick et al. | |
| 2005/0159711 A1 | 7/2005 | Kathrani et al. | |
| 2005/0251187 A1 | 11/2005 | Beane et al. | |
| 2006/0052750 A1 | 3/2006 | Lenker et al. | |
| 2006/0064159 A1 | 3/2006 | Porter et al. | |
| 2006/0094983 A1 | 5/2006 | Burbank et al. | |
| 2006/0100565 A1 | 5/2006 | Aboul-Hosn | |
| 2006/0135946 A1 | 6/2006 | Moehle et al. | |
| 2006/0135962 A1 | 6/2006 | Kick et al. | |
| 2006/0135963 A1 | 6/2006 | Kick et al. | |
| 2006/0135981 A1 | 6/2006 | Lenker et al. | |
| 2006/0184088 A1 | 8/2006 | Van Bibber et al. | |
| 2006/0200189 A1 | 9/2006 | Nance et al. | |
| 2006/0235357 A1 | 10/2006 | Woodward et al. | |
| 2006/0253102 A1 | 11/2006 | Nance et al. | |
| 2007/0016165 A1 | 1/2007 | Von Oepen et al. | |
| 2007/0088323 A1 | 4/2007 | Campbell et al. | |
| 2007/0197856 A1* | 8/2007 | Gellman et al. | 600/16 |
| 2008/0109058 A1 | 5/2008 | Greenberg et al. | |
| 2008/0200943 A1 | 8/2008 | Barker et al. | |
| 2008/0215008 A1 | 9/2008 | Nance et al. | |
| 2008/0243081 A1 | 10/2008 | Nance et al. | |
| 2009/0023975 A1 | 1/2009 | Marseille et al. | |
| 2009/0093873 A1 | 4/2009 | Navia | |
| 2009/0112049 A1 | 4/2009 | Ahmed | |
| 2009/0112050 A1* | 4/2009 | Farnan et al. | 600/16 |
| 2009/0254166 A1 | 10/2009 | Chou et al. | |
| 2009/0287182 A1 | 11/2009 | Bishop et al. | |
| 2009/0287183 A1 | 11/2009 | Bishop et al. | |
| 2010/0145267 A1 | 6/2010 | Bishop et al. | |
| 2010/0228077 A1 | 9/2010 | Lenker et al. | |
| 2010/0249491 A1 | 9/2010 | Farnan et al. | |
| 2011/0190567 A1 | 8/2011 | Farnan et al. | |

OTHER PUBLICATIONS

U.S. Patent and Trademark Office, International Preliminary Report on Patentability in corresponding PCT Application No. PCT/US11/24533, mailed May 16, 2012, 12 pp.

Douglas B. Cines et al, Endothelial Cells in Physiology and in the Pathophysiology of Vascular Disorders, Blood, 1998, 91:3527-3561.

U.S. Patent and Trademark Office, International Search Report and Written Opinion in PCT Serial No. PCT/US2011/024558, Jul. 1, 2011.

U.S. Patent and Trademark Office, International Search Report and Written Opinion in PCT Serial No. PCT/US2011/024533, Apr. 18, 2011.

U.S. Patent and Trademark Office, International Preliminary Report on Patentability in corresponding PCT Application No. PCT/US11/24558, Jul. 1, 2012.

U.S. Patent and Trademark Office, International Preliminary Report on Patentability in PCT Application No. PCT/US11/24558, Nov. 6, 2012.

U.S. Patent and Trademark Office, Final Office Action in U.S. Appl. No. 13/204,201, Nov. 21, 2012.

U.S. Patent and Trademark Office, International Search Report and Written Opinion in corresponding PCT Application No. PCT/US11/46772 mailed Dec. 8, 2011, 7 pp.

U.S. Patent and Trademark Office, Office Action in U.S. Appl. No. 13/204,201, Mar. 1, 2013.

U.S. Patent and Trademark Office, International Preliminary Report on Patentability in PCT Application Serial No. PCT/US11/46772, Jul. 29, 2013.

* cited by examiner

DEVICES, METHODS AND SYSTEMS FOR ESTABLISHING SUPPLEMENTAL BLOOD FLOW IN THE CIRCULATORY SYSTEM

CROSS-REFERENCE TO RELATED APPLICATION

This application claims the benefit of U.S. Provisional Patent Application Ser. No. 61/303,351, filed on Feb. 11, 2010, the disclosure of which is incorporated by reference herein.

TECHNICAL FIELD

This invention relates generally to medical devices and methods and, more particularly, to devices and methods for assisting conduction of bodily fluids.

BACKGROUND

Various devices and methods have been utilized to assist in conducting bodily fluids. For instance, blood pumps with inflow and outflow cannulae assist the heart in circulating blood in a patient experiencing congestive heart failure and a transplant organ has either not been located or the patient is not a suitable candidate for the transplant. Accordingly, the blood pump may be fluidically attached to the left side of the heart and then located remotely, such as subcutaneously or submuscularly in a manner similar to a pacemaker, in what is referred to as a "pump pocket." The pump pocket may be generally located at a position that is accessible by a surgical incision from below the collarbone, over the pectoral muscle, and toward the breast. A cannula may then be used to fluidically couple the heart to the pump. In still another example, a cannula is inserted into the bladder or kidney, such as in dialysis or urinary obstruction or infection.

Yet, known conventional cannula designs are susceptible to obstruction by adjacent biologic tissue. Therefore, there is a continuing need to develop cannulae to address these and other challenges associated with conventional cannulae and supplemental fluid flow systems.

SUMMARY

In one illustrative embodiment, the invention is directed to a cannula for insertion through a biological tissue. The cannula includes a shaft having proximal and distal end portions with a lumen therebetween. The cannula further includes a tip having a proximal end portion, a distal tip end, and a lumen therebetween. The proximal end portion of the tip is secured to the distal end portion of the shaft so that the lumen of the tip is in fluid communication with the lumen of the shaft. The tip includes an opening communicating with the lumen and extending proximally relative to the distal tip end to permit the flow of fluid into the lumen of the tip even in the event that the distal tip end becomes obstructed.

The opening that extends proximally may be at least one notch in the tip extending between the lumen and an outer surface of the tip, at least one aperture that extends between the lumen and the outer surface of the tip, an inclined edge that is angled relative to a lengthwise central axis of the tip, or a combination of the same.

In another illustrative embodiment, the invention is directed to a blood circulation assist system that includes the cannula, which extends from a pump to the heart of a patient. The assist system further includes an outflow cannula that extends from the pump to an artery of the patient.

In accordance with another illustrative embodiment, the invention is directed to a method of communicating fluid into a lumen of a cannula that includes a distal tip. The method comprises inserting the distal tip through a biologic tissue and into a cavity. Fluid is drawn from the cavity and into the tip through an opening in the distal tip of the cannula. The opening in the distal tip extends proximally relative to the distal tip end of the distal tip.

Yet another illustrative embodiment of the invention is directed to a method of preventing fluid flow obstruction in a cannula having a lumen and a distal tip. The method comprises inserting the distal tip through a biologic tissue and into a cavity. Fluid is drawn from the cavity and into the tip through an opening in the distal tip of the cannula. The opening in the distal tip extends proximally relative to the distal tip end of the distal tip. The fluid continues to be drawn from the cavity and into the lumen through the opening when the distal tip of the cannula is occluded by an adjacent biologic tissue.

DETAILED DESCRIPTION

Figure 1A:
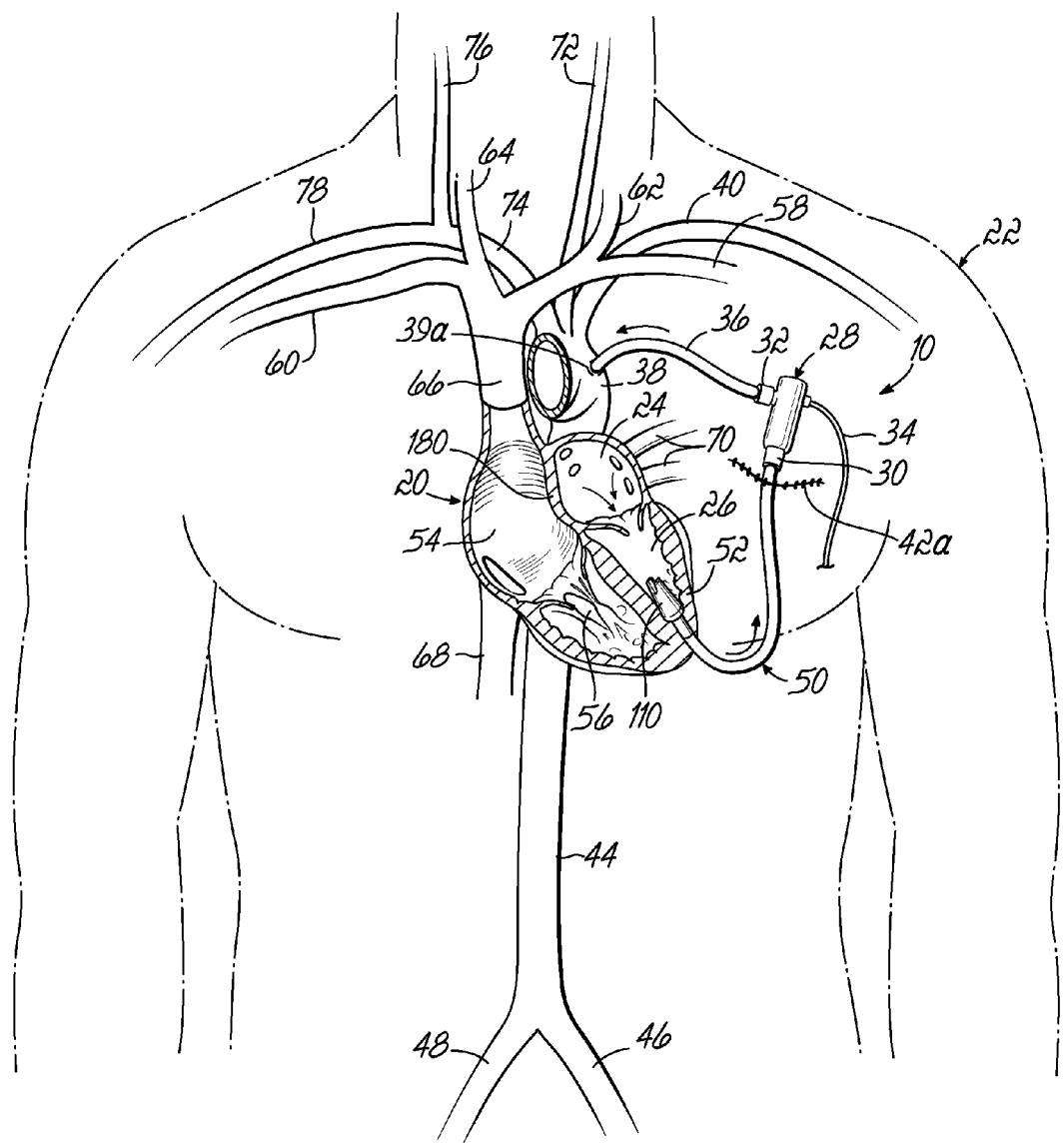
FIG. 1A is a schematic representation of chest anatomy and illustrates one example of a pathway, exterior to the vascular system, used to access a patient's heart and to implant a circulatory assist system that is coupled to the aortic arch in accordance with an embodiment of the invention.

FIG. 1A illustrates one of many possible general configurations of a blood circulation assist system 10. The devices and systems configured in accordance with the teachings herein may be implanted in any suitable surgical manner, including but not limited to those discussed generally herein, and may be used in association with other biologic tissues, for example, an interior chamber of a kidney (not shown) or still other biological tissues through which a cavity or chamber may be accessed and fluid withdrawn.

The system 10 may be used to pump blood from a chamber containing oxygenated blood of the heart 20 of a patient 22 (i.e., the left side at either the left atrium 24 or the left ventricle 26) and into the patient's arterial system, thereby "unloading" the heart 20 that has been weakened due to disease or genetic defect. The system 10 includes a blood pump 28 having an inlet 30 and an outlet 32. The pump 28 may be implanted in either the left or right side of the patient 22 (implantation in the left side is shown) or remain external to the patient's body. The pump 28 may include a power cord 34 that extends transdermally from the pump 28 to a position in the abdomen where the power cord 34 exits the patient 22 and connects to a power source (not shown). Various blood pump designs are known and may be used, including the conventional designs described in U.S. Pat. No. 6,176,848 issued to Rau et al. on Jan. 23, 2001, and entitled "Intravascular Blood Pump"; U.S. Pat. No. 6,116,862 issued to Rau et al. on Sep. 12, 2000, and entitled "Blood Pump"; U.S. Pat. No. 6,942,611 issued to Siess on Sep. 13, 2005, and entitled "Paracardiac Blood Pump"; U.S. Pat. No. 6,623,475 issued to Siess on Sep. 23, 2003, and entitled "Blood Pump Without Bearing"; and German Publ. No. DE102004019721 that was published on Oct. 6, 2005, and is entitled "Pump," the disclosures of which are incorporated herein by reference in their entireties.

Figure 1B:
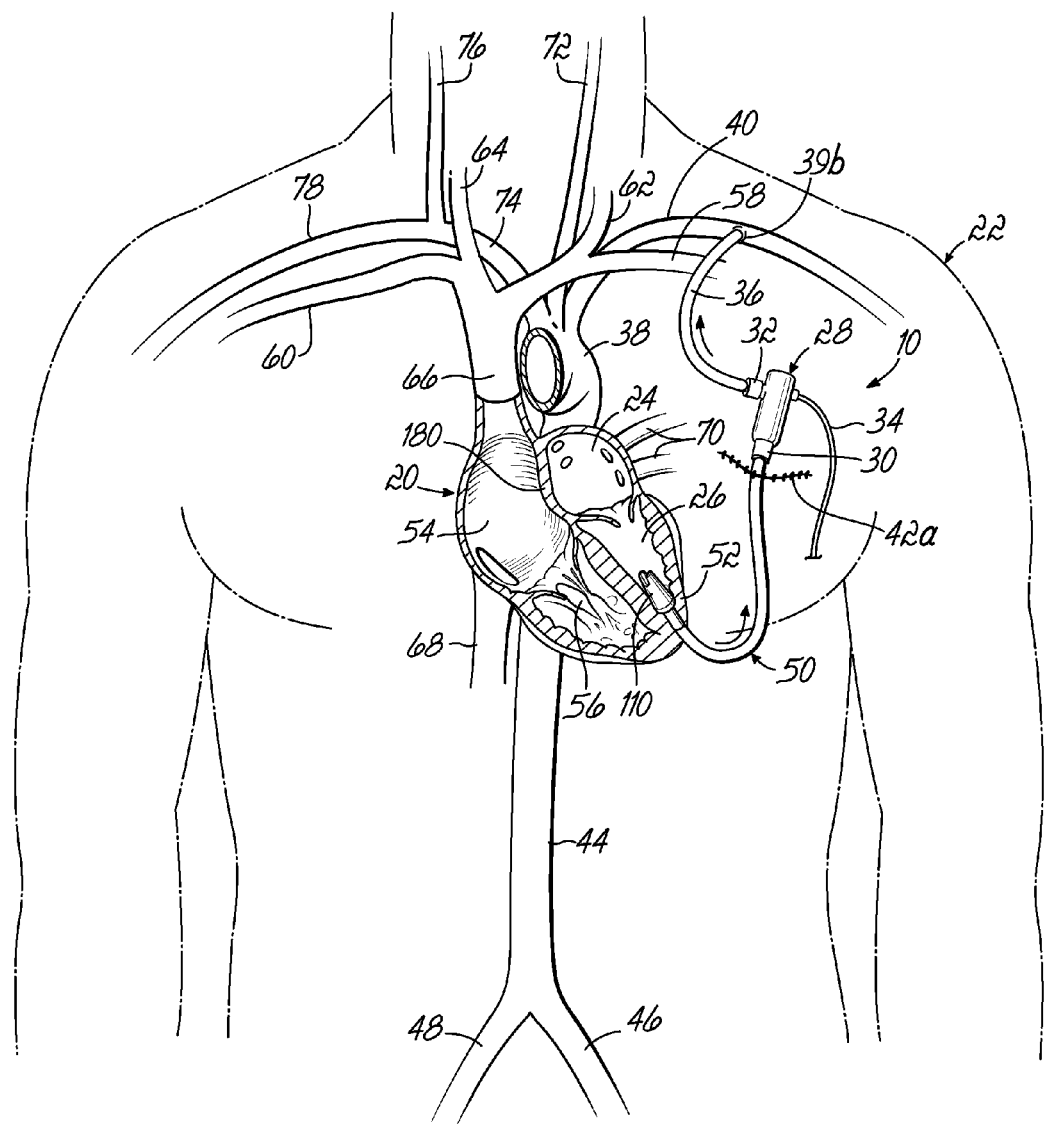
FIG. 1B is a schematic representation of another exemplary embodiment that is similar to FIG. 1A, but with the circulatory assist system coupled to the subclavian artery.
Figure 10:
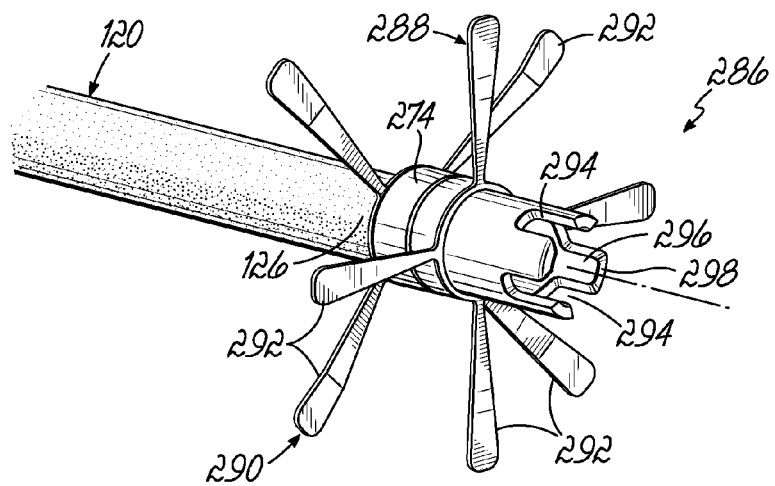
FIG. 10 is a perspective view of the inflow cannula including another transseptal embodiment of the cannula tip.

The system 10 further includes an outflow cannula 36 that connects the outlet 32 of the pump 28 to an artery, such as the aorta 38, at an arterial access site 39a, shown in FIG. 1A as being superior to the heart 20. Alternatively, the outflow cannula 36 may be connected to an arterial access site 39b that is located in the left subclavian artery 40, as shown in FIG. 1B. In the configurations shown in FIGS. 1A and 1B, the pump 28 may be superficially implanted in a pump pocket 42a. As another alternative and as shown in FIG. 10, the outflow cannula 36 may be connected to an arterial access site 39c in the descending aorta 44 and in close proximity to the left and right iliac arteries 46, 48. In this case, the pump 28 may be superficially implanted at a pump pocket 42b located in the abdomen of the patient 22. The outflow cannula 36 may be connected to the selected artery through a suitable surgical procedure that may involve the use of suitable grafts (not shown) and/or suturing (not shown).

Referring again to FIG. 1A, an inflow cannula 50 connects the inlet 30 of the pump 28 to an exterior wall of the heart 20, such as a wall 52 of the left ventricle 26. The inflow cannula 50 may be directed into the heart 20 through any desired surgical approach, such as one of the approaches subsequently discussed.

The outflow and inflow cannulae 36, 50 may be connected to the outlet 32 and inlet 30 of the blood pump 28, respectively, prior to or after implantation of the pump 28. In that regard, the cannulae 36, 50 may be first cut to a suitable length by an appropriate sterilized cutting tool (not shown) such that the system 10 may be more easily implanted without kinking of the cannulae 36, 50. The inflow cannula 50 may be configured to facilitate cutting to the desired length, as subsequently discussed.

In operation, blood may be pumped from the left ventricle 26, through the inflow cannula 50 to the pump 28, and from the pump 28 to the selected artery (the aorta 38 in FIG. 1A, the left subclavian artery 40 in FIG. 1B, the descending aorta 44 in FIG. 10, or other as desired).

For illustrative and reference purposes, certain additional anatomy is shown, including a right atrium 54 and a right ventricle 56 on the right side of the heart 20. The right atrium 54 receives blood from the venous network, generally, and more specifically, as shown, the left and right subclavian veins 58, 60, the left and right jugular veins 62, 64, and the superior and inferior vena cavae 66, 68. Blood moves from the right atrium 54 to the right ventricle 56 and is then pumped to the lungs (not shown) to be oxygenated. Blood returning from the lungs enters the left atrium 24 of the heart 20 through the pulmonary veins 70. The blood within the left atrium 24 moves into the left ventricle 26 and is pumped into the aorta 38 and the arterial system beyond, including the left subclavian artery 40, the left common carotid 72, and the brachiocephalic trunk 74 leading to the right common carotid 76 and the right subclavian artery 78.

Figure 2:
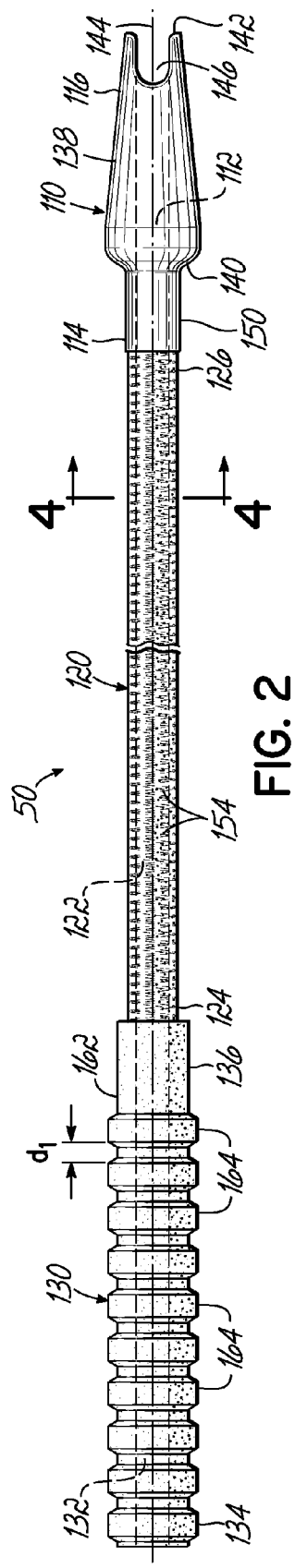
FIG. 2 is a side-elevational view of one exemplary embodiment of an inflow cannula having a cannula tip.

Turning now to FIG. 2, and with continued reference to FIG. 1A, the inflow cannula 50 is shown in greater detail. The inflow cannula 50 includes a tip 110 that is configured to be inserted through a biologic tissue, such as the wall 52 of the left ventricle 26. The tip 110 includes a lumen 112 extending between proximal and distal end portions 114, 116. The inflow cannula 50 also includes a shaft 120 having a lumen 122 extending between proximal and distal end portions 124, 126. The inflow cannula 50 still further includes a hub 130 having a lumen 132 extending between proximal and distal end portions 134, 136. The distal end portion 126 of the shaft 120 is coupled to the proximal end portion 114 of the tip 110, and the proximal end portion 124 of the shaft 120 is coupled to the distal end portion 136 of the hub 130. The hub 130 may be molded directly to the proximal end portion 124 of the shaft 120 or, alternatively, the hub 130 may be constructed separately and then affixed to the proximal end portion 124 with a biocompatible adhesive. The lumens 112, 122, 132 align to be collinear and in fluidic communication. The lumens 112, 122, 132 may have the same diameter to eliminate steps or other discontinuities in order to minimize thrombus formation and flow restriction therein.

Figure 1C:
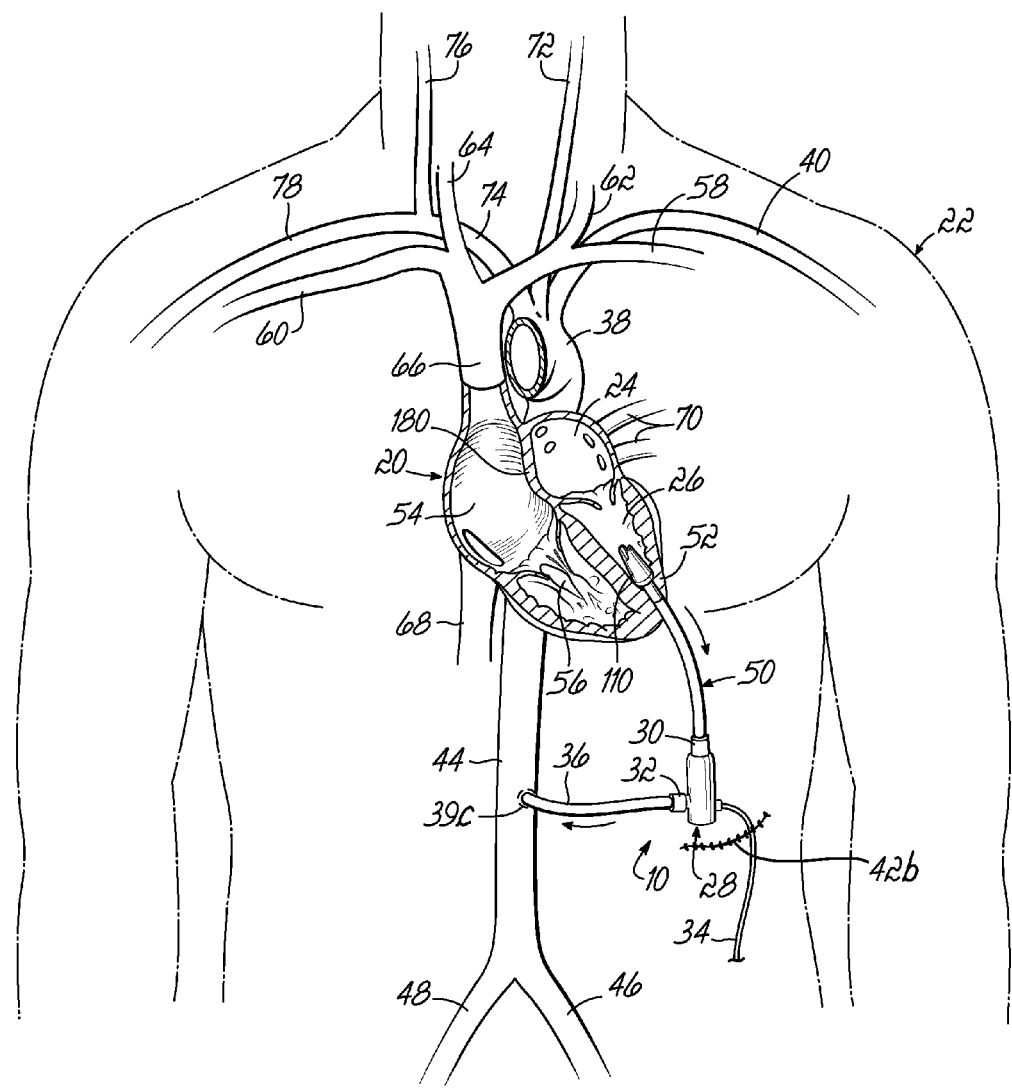
FIG. 1C is a schematic representation of yet another exemplary embodiment that is similar to FIG. 1A, but with the circulatory assist system coupled to the descending aorta at a location inferior to the heart and in close proximity to the iliac arteries.

The proximal end portion 134 of the hub 130 may be configured to be coupled to the inlet 30 of the blood pump 28, as shown in FIG. 1A, and such that blood may flow from the left ventricle 26 of the heart 20, through the lumens 112, 122, 132 and to the inlet 30 of the blood pump 28. The blood may then be pumped through the outflow cannula 36 to the desired artery, such as the aorta 38, descending aorta 44, or the left subclavian artery 40 as described previously in conjunction with FIGS. 1A, 1B, and 1C.

The tip 110 may be constructed from a metallic material, such as titanium, a titanium alloy, stainless steel, or platinum. The tip 110 when constructed from a metallic material may include a sintered section or at least a portion covered by a fabric that promotes the in-growth of tissue. Alternatively, the tip 110 may be molded from a thermoset material, such as silicone, or a thermoplastic material, such as polyurethane. An example of a polyurethane that may be used is CARBOTHANE (Lubrizol Advanced Materials, Inc., Cleveland, Ohio). If a relatively conformable design is desired, the tip 110 may be constructed from a thermoset or thermoplastic material having a durometer ranging from about shore 25 A to about shore 90 A. If a relatively rigid design is desired, the tip 110 may be constructed from a thermoset or thermoplastic material having a durometer ranging from about shore 55 D to about shore 90 D.

To further minimize the chance of thrombus formation, the molding process may include an insert molding process that eliminates parting lines, i.e., those places where a mismatch of material may occur. Use of the insert molding process results in a luminal surface, which is in direct contact with blood flowing through the tip 110, that is smooth and seamless. Accordingly, it is not necessary to coat an inner surface of the lumen 112 with an anti-thrombotic material, yet the coatings may be included if so desired.

To increase hemocompatibility, the distal end portion 116 of the tip 110 may be polished to minimize irregularities resulting from the machining process. The highly polished surface minimizes proliferation of tissue growth, hence minimizing the likelihood that tissue will grow over the tip 110 and occlude blood flow into the inflow cannula 50.

Figure 3:
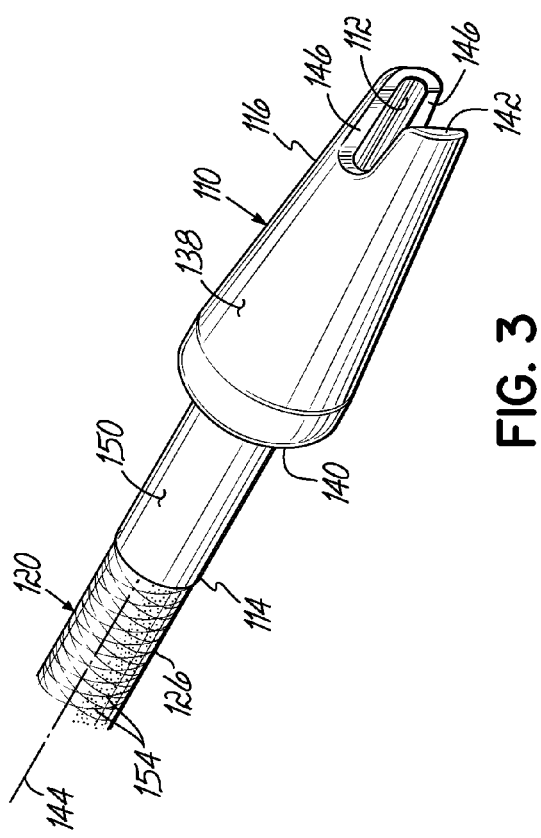
FIG. 3 is an enlarged perspective view of the cannula tip shown in FIG. 2.

Referring still to FIG. 2 and now also to FIG. 3 where additional details of the tip 110 may be seen. The distal end portion 116 of the tip 110 is configured to be inserted into a chamber of the patient's heart 20 (FIG. 1A). In that regard, while the diameter of the lumen 112 may be constant throughout the length of both the proximal and distal end portions 114, 116 of the tip 110, an outer surface 138 of the tip 110 may be discontinuous. One such discontinuity, a shoulder 140, may be positioned between the proximal and distal end portions 114, 116 and is configured to be positioned against an inside surface of the wall 52 (FIG. 1A) of the heart 20 (FIG. 1A) when the distal end portion 116 is inserted into, for example, the left ventricle 26 (FIG. 1A). This controls the length of the distal end portion 116 inserted in the chamber and ensures that the distal end portion 116 is not dislodged from the chamber prior to suturing of the tip 110 to the wall 52 (FIG. 1A) of the heart 20 (FIG. 1A).

The outer surface 138 may converge, or taper, such as a frusto-conical shape, between the shoulder 140 and the distal end portion 116 to distal tip end 142. The distal tip end 142 may be constructed, or molded, as shown, to be substantially orthogonal to a lengthwise central axis 144 of the tip 110. This arrangement permits blood to be continuously withdrawn from the left ventricle 26 (FIG. 1A); however, a variety of alternative structure are possible, including the subsequently discussed alternative tips.

The tip 110 further includes an opening 146 extending proximally relative to the distal tip end 142 that is configured to permit blood to be continuously drawn into the lumen 112 of the tip 110, even when the distal tip end 142 of the tip 110 becomes obstructed or occluded, such as by adjacent internal heart tissue. The opening 146 may include a variety of shapes, shown here as two notches 146, that are in fluid communication with the lumen 112. The two circumferentially-spaced (illustrated as diametrically opposed) notches 146 extend longitudinally and proximally from the distal tip end 142 and between the lumen 112 and the outer surface 138 of the tip 110, radially. While the particular illustrative embodiment of FIGS. 2 and 3 includes two notches 146, it would be understood that any numbers of openings 146, or apertures, of various shapes or sizes may be used. The size and number of the notches 146 may be selected so that the summed total cross-sectional area of all notches 146 is about the same as, or greater than, the smallest cross-sectional area of the lumen 112. This configuration avoids a reduction in the flow of blood in the event that the distal tip end 142 becomes obstructed or occluded during pump operation. Whether or not such blockage occurs is a function of the proximity of the distal tip end 142 to the inside surface of the biologic tissue through which the tip 110 extends and the minimum hydrostatic pressure within the chamber as blood is pumped into the inflow cannula 50. More particularly, a drop in the chamber's hydrostatic pressure during pump operation may cause the chamber to sufficiently collapse such that the biologic tissue contacts the tip 110 and at least partially obstructs the distal tip end 142. If such a block should occur with a tip constructed in accordance with an embodiment with the present invention, then continued operation of the pump 28 may proceed by the influx of blood to the lumen 112 via the notches 146. Therefore, an undesirable interruption in the flow of blood into the inflow cannula 50 may be avoided.

An outer surface 150 of the proximal end portion 114 may be polished, sintered, or coated with a material that promotes, or accelerates, wound healing of the biologic tissue in contact with the outer surface 150 when the tip 110 is inserted into the biologic tissue. Suitable materials may include, but are not limited to, calcium phosphate and collagen. The portions of the outer surface 138 of the tip 110 that are exposed to blood may include an anti-thrombotic coating to minimize thrombus formation. Examples of anti-thrombotic coating materials that may be used include, but are not limited to, heparin, and silver.

Figure 4:
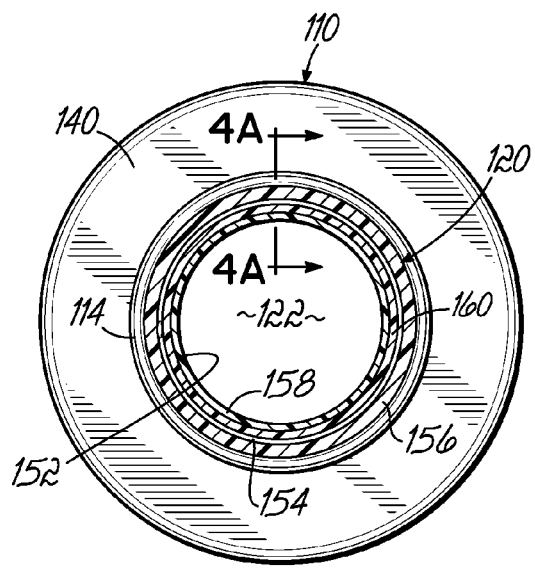
FIG. 4 is a cross-sectional view through the diameter of the inflow cannula, taken along the line 4-4 in FIG. 2.
Figure 4A:
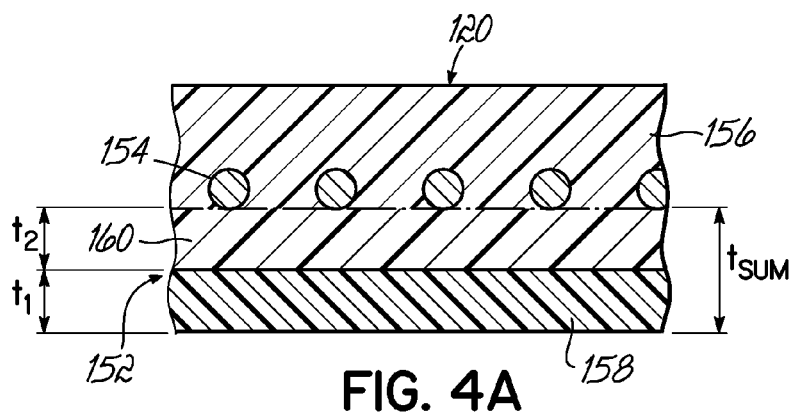
FIG. 4A is a cross-sectional view of an inner liner of the inflow cannula, taken along the line 4A-4A in FIG. 4.

Referring now to FIGS. 2-4, the shaft 120 may be secured to the tip 110 and the hub 130 by thermal bonding, a molding process, or by other means, such as the application of sufficient temperature and pressure to the parts to be bonded. The shaft 120 may be constructed as a unitary structure with the tip 110, and the hub 130 thermally bonded thereto. Alternatively, the shaft 120 may have a composite construction, an example of which is shown in the cross-sectional view in FIG. 4. In the illustrative embodiment, the shaft 120 may include an inner liner 152, a reinforcing structure 154 that is secured to the inner liner 152, and an outer jacket 156 that is secured to both the reinforcing structure 154 and the inner liner 152. Accordingly, and as shown in FIG. 4A, the inner liner 152 may be tubular and defines the lumen 122 of the shaft 120. The inner liner 152 may be a co-extruded liner having inner and outer portions 158, 160, which combine to define a wall thickness (designated as $t_{sum}$) of the inner liner 152. The inside diameter of the inner portion 158, which corresponds to the diameter of the lumen 122, may vary depending upon the desired blood flow rate for the particular application. Generally, the lumen 122 will have the same diameter as the lumen 132 of the hub 130 and the lumen 112 of the tip 110. For example, the diameter of the lumen 122 may vary from about 0.040 inch (1.016 mm) to about 0.400 inch (10.016 mm). The overall wall thickness of the shaft 120 may vary depending upon the desired mechanical performance characteristics (bending, column strength, torsional strength, etc.) of the shaft 120. For example, the wall thickness of the shaft 120 may vary from about 0.004 inch (0.1016 mm) to about 0.080 inch (2.032 mm).

The inner portion 158 of the inner liner 152 may be constructed from a thermoset material or a thermoplastic material having a relatively high durometer, for example, ranging from about shore 55 D to about shore 80 D and with a thickness, $t_1$, that may range from about 0.0005 inch (0.0127 mm) to about 0.0050 inch (1.27 mm). Suitable thermoset materials may include, but are not limited to, an etched fluropolymer and polyimide. Examples of suitable thermoplastic materials include, but are not limited to polyamide, polyurethane, and polyethylene. An example of a polyurethane that may be used is CARBOTHANE.

The outer portion 160 of the inner liner 152 may be constructed from a thermoplastic material having a lower durometer, for example, ranging from about shore 25 A to shore 60 A, and a thickness, $t_2$, that may range from about 0.0005 inch (0.0127 mm) to about 0.0100 inch (0.254 mm). An example of a suitable material that may be used is a polyurethane, such as CARBOTHANE.

The reinforcing structure 154 may be overlayed onto the outer portion 160 of the inner liner 152 and may have a braided construction as shown in FIG. 3 or a coiled construction as shown in FIG. 2. The reinforcing structure 154 may be constructed from a metal wire, such as stainless steel or titanium wire, but may also be made from a polymeric material, such as KEVLAR (E.I. du Pont de Nemours and Co., Wilmington, Del.). Further, the construction material may have various cross-sectional shapes, including, but not limited to, round and rectangular. If a round wire is used, the wire diameter may typically vary from about 0.001 inch (0.0254 mm) to about 0.005 inch (0.127 mm). If the material used has a rectangular cross-section, the rectangle may typically have a height ranging from about 0.001 inch (0.0254 mm) to about 0.005 inch (0.127 mm) and a width ranging from about 0.003 inch (0.0762 mm) to about 0.010 inch (0.254 mm).

The coiled construction of FIG. 2 may include a coil pitch ranging from about 0.001 inch (0.0254 mm) to about 0.060 inch (1.524 mm), depending on the particular wire used and the diameter of the lumen 122. In some embodiments, the coil pitch may vary along the length of the shaft 120 with the higher coil pitch being located distally to increase flexibility distally. With a braided construction, shown in FIG. 3, the braid pic rate (i.e., the number of cross-overs per inch of braid) may range from about 10 ppi to about 100 ppi; in some embodiments, the pic rate may vary along the length of the shaft 120 with higher pic rates positioned distally, again for increased flexibility.

The outer jacket 156 is applied over the inner liner 152 and the reinforcing structure 154 to complete the composite construction. The outer jacket 156 may be constructed from a thermoplastic material, such as a polyurethane, having a durometer ranging from about shore 25 A to about shore 60 A. The material of the outer jacket 156 is selected to be compatible with the materials of the outer portion 160 of the inner liner 152 and of the reinforcing structure 154. This attention to compatibility ensures complete encapsulation of the reinforcing structure 154 and complete polymeric bonding between the outer jacket 156 and the inner liner 152, which prevents de-lamination.

In some embodiments, the inner and outer portions 158, 160 may be constructed from similar, or the same, material; however, this is not required.

Though not specifically shown, the shaft 120 may include barbs and/or a cannula stop that aid in the assembly of the tip 110 to the shaft 120. The barbs provide an interference fit between the shaft 120 and the tip 110, while the stop ensures complete insertion of the shaft 120 into the tip 110.

Referring still to FIG. 2 where one exemplary embodiment of the hub 130 is shown and includes an inner cylindrical portion 162 that extends from the proximal end portion 134 to the distal end portion 136. The hub 130 may further include a plurality of longitudinally-spaced, annular members 164 that are integral with, and extend around, the cylindrical portion 162. The annular members 164 control a kink radius of the hub 130 and allow a physician to trim the length of the hub 130 to conform to the particular anatomy of the patient 22. The kink radius may be considered to be the bend radius of the shaft 120 that would result in a local deformation, or kinking, of the shaft 120. In FIG. 2, the annular members 164 are spaced equally by a predetermined distance, $d_1$. The physician may trim the hub 130 to the required length by cutting the cylindrical portion 162 between adjacent ones of the annular members 164 to provide the desired length of the hub 130. The distal end portion 136 of the hub 130 may be devoid of the annular members 164 in order to facilitate bonding of the distal end portion 136 of the hub 130 to the proximal end portion 124 of the shaft 120.

Figure 5:
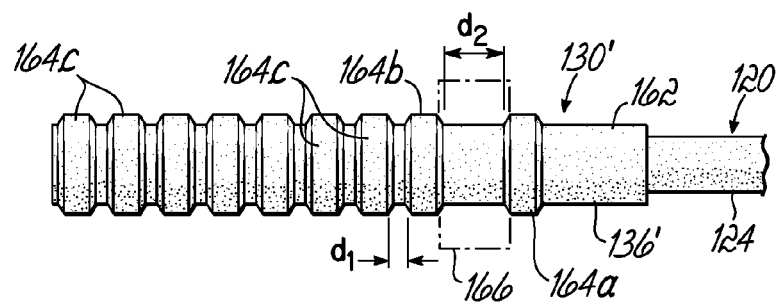
FIG. 5 is a side-elevational view of a hub of the inflow cannula shown in FIG. 2.

FIG. 5 illustrates an alternative embodiment of a hub 130' that includes a distal-most annular member 164a that is longitudinally-spaced from the adjacent annular member 164b by a distance, $d_2$, that is greater than $d_1$, defined above. The size of $d_2$ may be selected to accommodate a flow sensor 166, shown in phantom, which may be used to measure the blood flow rate through the inflow cannula 50. The flow sensor 166 may be any commercially available product, such as the flow meters that are commercially available from Transonic Systems, Inc. (Ithaca, N.Y.), that circumvent the hub 130, and that operate by an ultrasonic technology. The flow sensor 166 may be clipped, or otherwise secured, to the hub 130. Wires or cables associated with the flow sensor 166 may be routed with the power cord 34 (FIG. 1A) associated with the pump 28 (FIG. 1).

The construction material of the hub 130 may be selected from known materials, for example, a thermoset material such as silicone, or a thermoplastic material, such as polyurethane. The selected material may have a durometer that varies from about shore 25 A to about shore 75 A and may have a stiffness generally equivalent to, or greater than, the overall stiffness of the composite structure of the shaft 120. The hub 130 may then be molded or bonded to the proximal end portion 124 of the shaft 120.

One illustrative procedure for connecting the inflow cannula 50 to the heart 20 is shown in FIGS. 6A-6D with additional reference made to FIG. 1A. While the method includes the tip 110 from FIG. 2, it would be understood that any design, including those illustrated herein, may be incorporated.

Figure 6A:
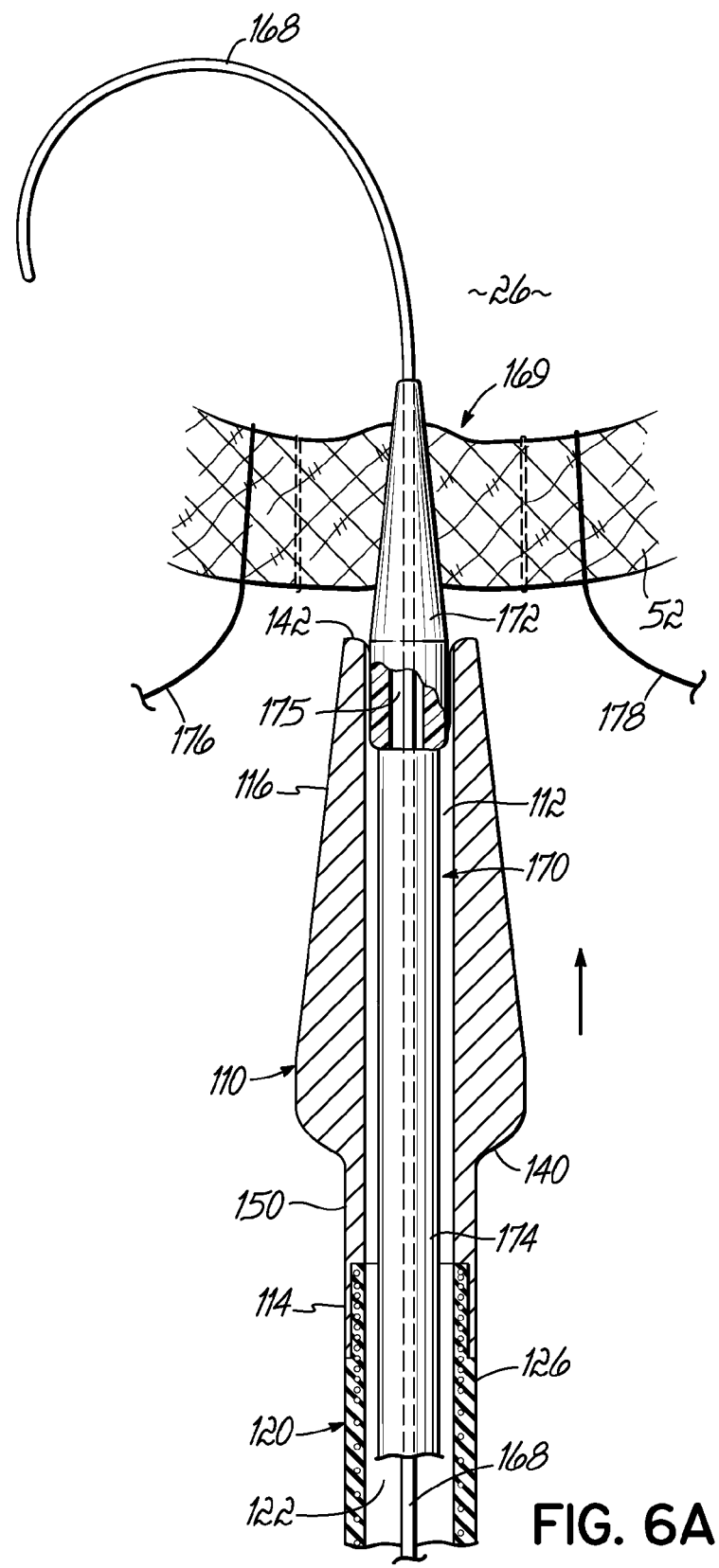
FIGS. 6A-6D are enlarged cross-sectional views illustrating successive steps of an exemplary method of surgically implanting a cannula tip into the left ventricle of the heart.

In FIG. 6A, the physician punctures the wall 52 with a guide-wire 168 at a surgical site 169. A dilator device 170, which includes a tip 172 that is secured to a shaft 174 having a lumen 175 configured to accept the guide-wire 168, is backloaded over the guide-wire 168 and delivered to the wall 52 of the heart 20. The inflow cannula 50 is backloaded over the dilator device 170 and advanced to the wall 52 of the heart 20.

As FIG. 6A illustrates, a distal portion of the guide-wire 168 may be looped, coiled, or j-shaped, at least partially, to help avoid trauma to the tissue of the heart 20 during and after insertion.

The tip 172 of the dilator device 170 generally includes a conical shape that may be used to gradually dilate a puncture in the wall 52 that was created by the guide-wire 168. This gradual dilation facilitates the insertion of the tip 110 through the wall 52. Insertion is further facilitated by the frusto-conical shape of the distal end portion 116 of the tip 110.

Figure 6B:
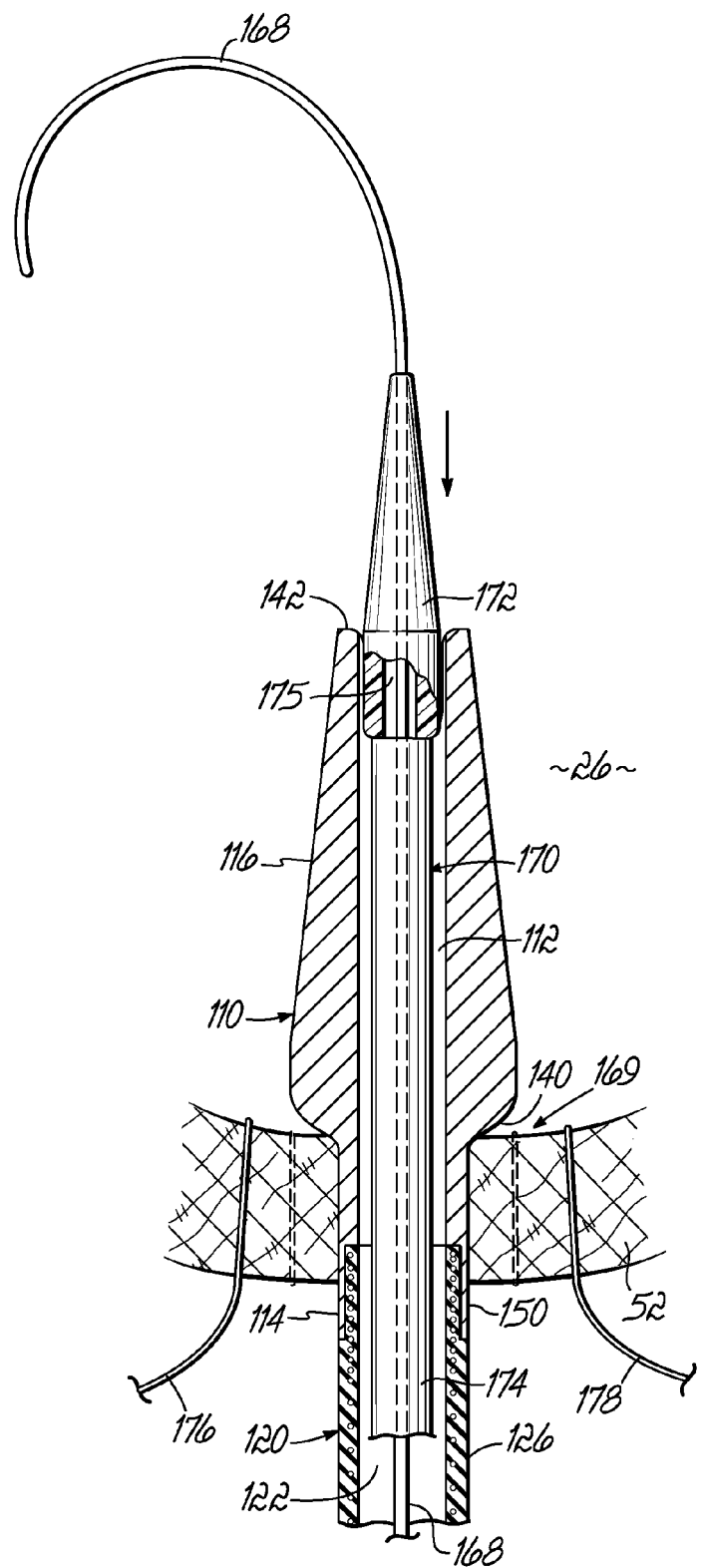

FIG. 6B illustrates a subsequent step with the entire distal end portion 116 of the tip 110 inserted into the left ventricle 26. After insertion, the inflow cannula 50 may be retracted slightly so that the shoulder 140 of the tip 110 is positioned against the inside surface of the wall 52, acting as a firm stop and providing a perceptible feedback to the physician.

Figure 6C:
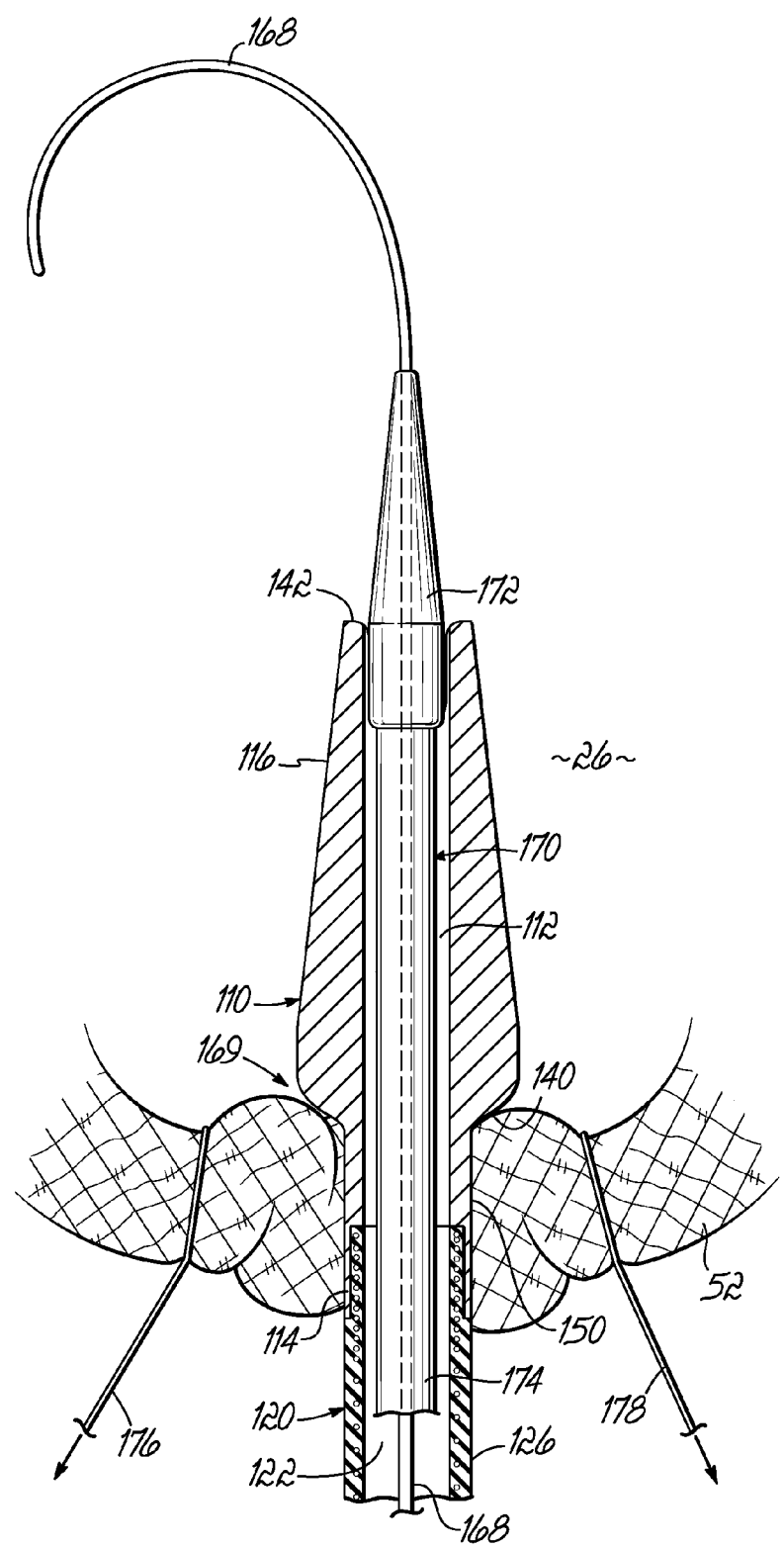

With the tip 110 so positioned, purse string sutures 176, 178 may be used to tie off and fully secure the inflow cannula 50 to the wall 52, as shown in FIG. 6C. If necessary, additional tissue may be gathered with additional purse string sutures (not shown), though this is not specifically shown. As discussed previously, the outer surface 150 of the proximal end portion 114 of the tip 110, which extends across the puncture in the wall 52, may be coated with a material that promotes, or accelerates, wound healing of the vascular tissue that is in contact with the outer surface 150. This may further aide in providing a leak tight seal.

Figure 6D:
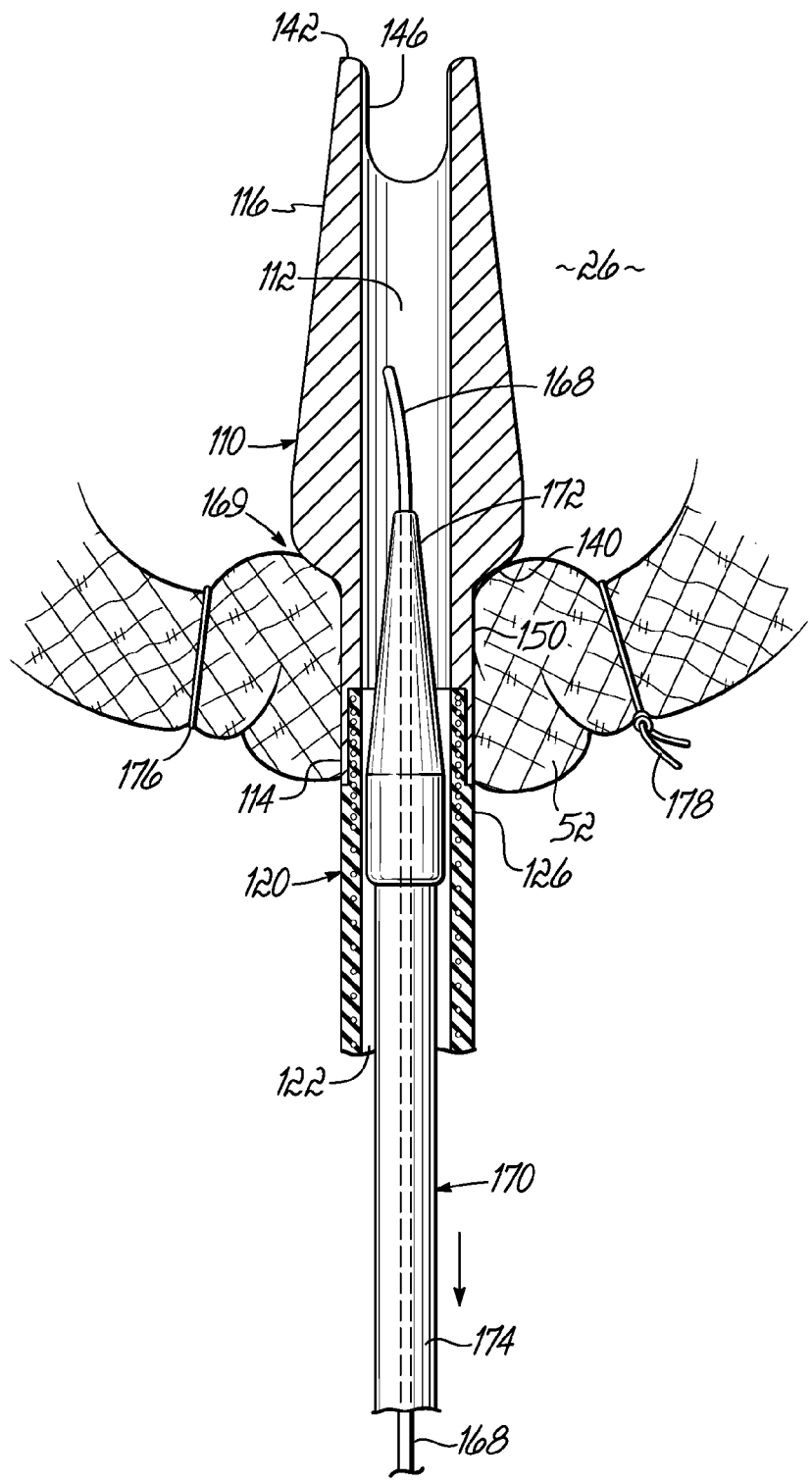

FIG. 6D illustrates the surgical site 169 after the sutures 176, 178 have been tightened and the dilator device 170 with the guide-wire 168 are retracted from the left ventricle 26. As a result, the distal end portion 116 of the tip 110 remains inserted in the left ventricle 26 and is secured to the wall 52 of the heart 20.

It will be readily appreciated that the procedure illustrated in FIGS. 6A-6D is a just one exemplary surgical based procedure for inserting the tip 110. Alternatively, the procedure could include a lateral thoracotomy to access the left atrium 24 so that the tip 110 is anchored at a location on the posteromedial wall, near an intra-atrial septum 180, at the so called "Waterson's Groove"; a thoracoscopic surgery where a tubular trocar is used to access the intra-thoracic location (Waterson's Groove, for example); or an over-the-wire (Seldinger) technique where a needle crosses the intra-atrial septum 180, a guide-wire may be placed therethrough, and a specialized introduction obtuator (or a dilator device) may be used in advancing the inflow cannula 50 into the intra-atrial septum 180, as described in greater detail below.

Figure 7:
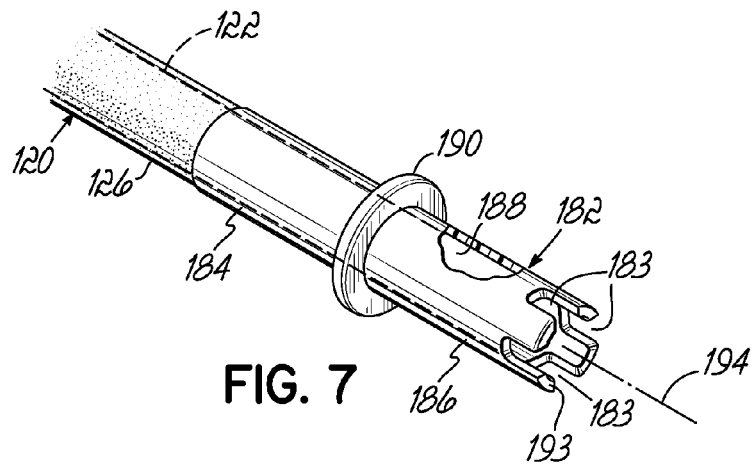
FIG. 7 is a perspective view of the inflow cannula including another embodiment of a cannula tip.

One of ordinary skill would readily appreciate that the opening extending proximally relative to the distal tip end may be constructed to include any number of alternate configurations beyond the embodiment shown in FIGS. 2-3. For example, FIG. 7 illustrates a tip 182 that, like the tip 110 of FIGS. 2-3, includes at least one opening 183 configured to permit a continuous flow of blood even in the event of partial or complete blockage or occlusion. In that regard, the tip 182 includes proximal and distal end portions 184, 186 with a lumen 188 extending therebetween and may be constructed and manufactured similarly to the tip 110 of FIG. 3. The proximal and distal end portions 184, 186 may be separated by an annular member, or seating ring 190, that is configured to operate in a manner that is similar to the shoulder 140 of the tip 110 shown in FIG. 3, i.e., as a positive stop during insertion. The proximal end portion 184 is secured to the distal end portion 126 of the shaft 120, as described previously, and such that the lumen 188 of the tip 182 is in fluid communication with the lumen 122 of the shaft 120.

The at least one opening 183 is defined by a plurality of notches, i.e., openings 183 extending proximally from the distal tip end 193, and indeed being coextensive with the distal end tip 193. Accordingly, the distal tip end 193 may be constructed to be substantially perpendicular to a lengthwise central axis 194. In the illustrative embodiment, the notches 183 are equally spaced circumferentially; however, this spacing arrangement is not required. Further, while four notches 183 are shown, it would be understood that the number of notches 183 may vary from two (shown in FIG. 3) to eight and would depend on the cross-sectional area of the lumen 188, the lengths of the notches 183, and/or the widths of the notches 183. Stated another way, the number and configuration of the notches 183 may be selected such that the total cross-sectional flow area of all notches 183 is approximately the same as the cross-sectional area of the lumen 188 in order to avoid restriction of blood flow.

Figure 8:
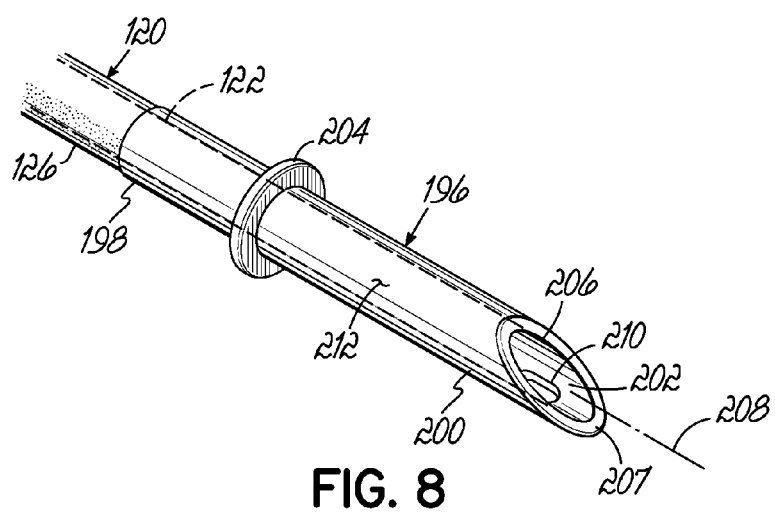
FIG. 8 is a perspective view of the inflow cannula including yet another embodiment of a cannula tip.
Figure 8A:
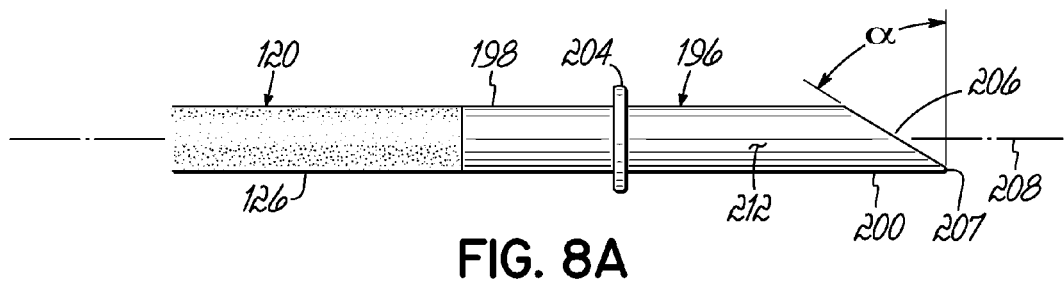
FIG. 8A is a side-elevational view of the cannula tip shown in FIG. 8, depicting the angle of inclination of a distal end surface of the cannula tip.

FIGS. 8 and 8A illustrate yet another embodiment of a tip 196 that includes proximal and distal end portions 198, 200 with a lumen 202 extending therebetween. As stated before, the proximal end portion 198 is secured to the distal end portion 126 of the shaft 120 such that the lumen 202 of the tip 196 is in fluid communication with the lumen 122 of the shaft 120. Further, and similar to the tip 182 of FIG. 7, the tip 196 may include a seating ring 204 separating the proximal and distal end portions 198, 200 and is configured to be positioned against the inside surface of a tissue wall 52 (FIG. 1A).

In the illustrative embodiment, the opening 206 in the tip 196 is defined by an inclined edge that extends proximally from a distal tip end 207 of the tip 196. The degree of inclination may be an angle, $\alpha$, that varies relative to a longitudinal centerline axis 208 of the tip 196 from about 15° to about 75°.

The distal end portion 200 includes a second opening 210 extending proximally relative to the distal tip end 207, shown herein as an aperture 210 that is enclosed by the material comprising the tip 196 and that extends between the lumen 202 and an outer surface 212 of the tip 196. While only one aperture 210 is shown, it would be understood that the distal end portion 200 may alternatively include a plurality of apertures.

During normal pump operation, the likelihood that the inclined edge 206 would become blocked is significantly reduced. In this manner, the proximally extending opening 206 will help to assure blood flow into the lumen 202. However, should the blood flow through the inclined edge 206 be reduced, then blood flow may continue through the second opening 209, the aperture 210. In this way, the tip 196 provides two manners of preventing blood flow reduction.

In still other embodiments, a tip may be constructed in a manner that reduces the need for purse string sutures. Additionally, and/or optionally, a tip may be constructed in a manner that facilitates use in a less-invasive, catheter-based surgical procedure, such as those described in U.S. patent application Ser. No. 12/256,911, published as U.S. Patent Appl. Publ. No. 2009/0112050 and entitled "Transseptal Cannula, Tip, Delivery System, and Method," the disclosure of which is incorporated herein by reference in its entirety.

Figure 9:
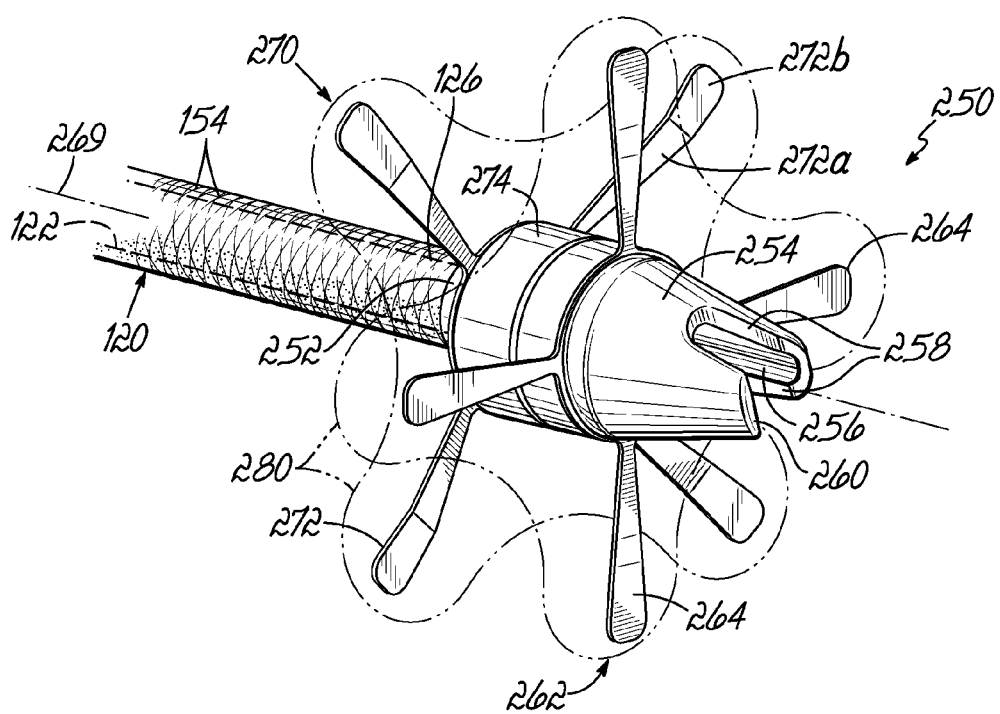
FIG. 9 is a perspective view of the inflow cannula including another embodiment of a cannula tip for use in a trans-septal procedure.

One exemplary embodiment of a suitable tip design is shown in FIG. 9 and includes a tip 250 having a truncated frusto-conical shape that is similar to the shape described previously with reference to FIG. 3. The tip 250 has a proximal end 252 and a distal end 254 with a lumen 256 extending therebetween that is collinear with the lumen 122 (FIG. 2) of the shaft 120. The distal end 254 includes at least one opening 258, defined in FIG. 9 as two notches, that extend proximally from a distal tip end 260.

Figure 9A:
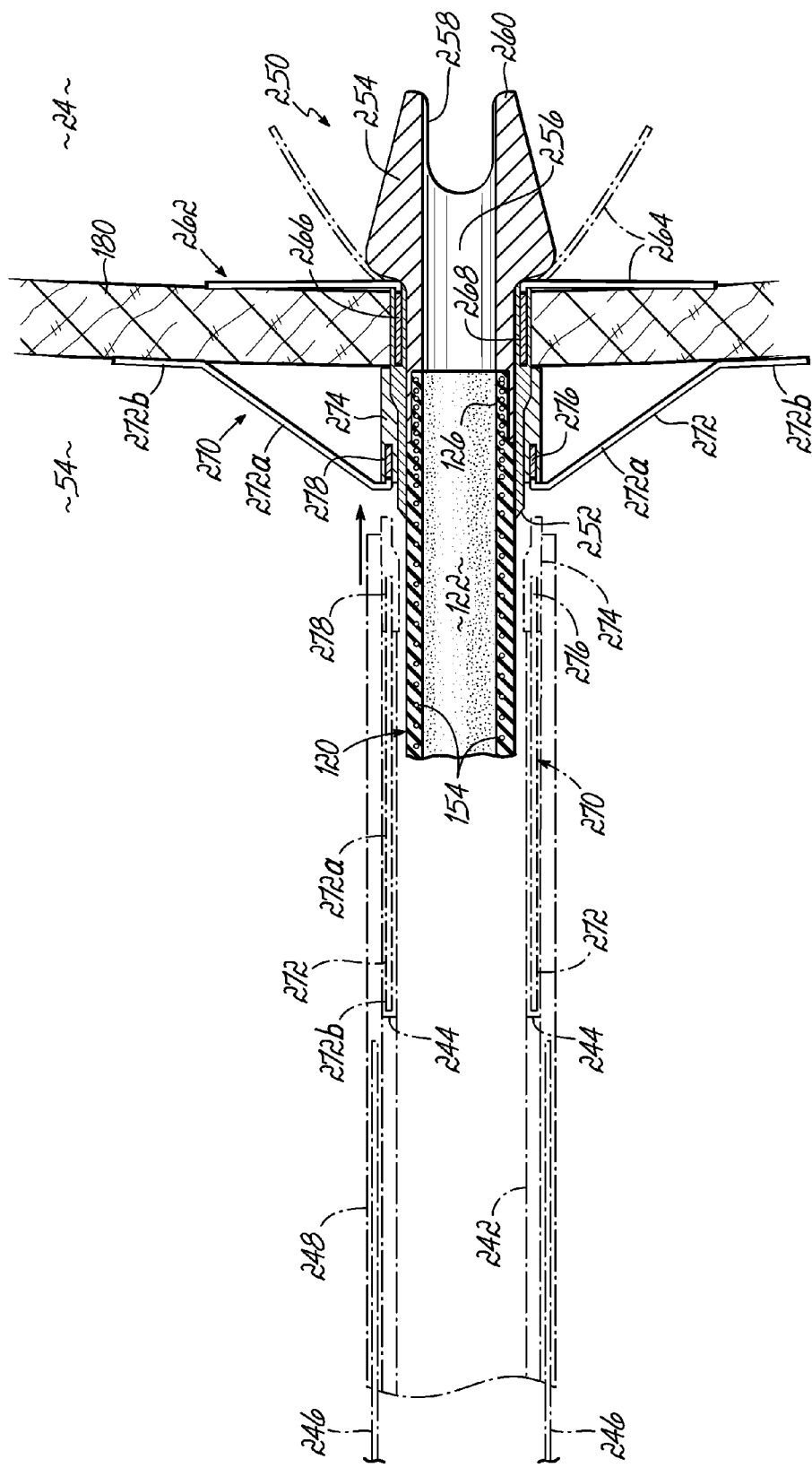
FIG. 9A is an enlarged cross-sectional view of the cannula tip of FIG. 9 implanted across the intra-atrial septum.

Referring still to FIG. 9 and also now to FIG. 9A, the tip 250 further includes a first anchor 262 having a plurality of struts 264 as described in U.S. patent application Ser. No. 12/720,012, published as U.S. Patent Appl. Publ. No. 2010/0249490 and entitled "Transseptal Cannula Device, Coaxial Balloon Delivery Device, and Methods of Using the Same," the disclosure of which is incorporated herein by reference in its entirety. It should be appreciated that while four struts 264 are shown, this number is not so limited but rather an anchor could be envisioned where fewer or more struts may be necessitated or desired for a particular physician's needs or preference. Yet, providing at least three struts 264 may result in greater stability of the implanted tip 250.

The struts 264 of the first anchor 262 may be at least partially constructed from a superelastic NiTi material by chemically etching the parts from flat sheet stock, electropolishing the etched parts to remove rough edges generated during the formation process, and then heating the parts to a superelastic state. However, other suitable biocompatible, non-compliant, flexible material would be sufficient. As is shown, the struts 264 extend from a common ring structure 266 that is affixed into a groove 268 within the tip 250 with glue, epoxy, friction fit, or other known means. As a result, the struts 264 of the first anchor 262 may extend radially, in a deployed position, from the common ring structure 266 and relative to the lengthwise central axis 269. In this deployed position, the first anchor 262 is configured to be positioned along a first side of the biologic tissue, shown here as the intra-atrial septum 180 between the right and left atria 54, 24. The superelastic state of the struts 264 allows the struts 264 to be deflected to a collapsed position (shown in phantom) that is directed angularly away from the deployed position (shown in solid). This collapsible nature of the first anchor 262 enables the tip 250 to be preloaded into a delivery sheath (not shown) and reduces the invasiveness of the procedure. More specifically, the struts 264 of the first anchor 262 are deflected in a distal direction and the inflow cannula 50 back-loaded into the delivery sheath. The distally directed struts 264 are thus positioned for deployment, as shown in phantom in FIG. 9A. If desired, a balloon catheter may be directed through the lumen of the shaft 120 and the tip 250. The balloon, when inflated contacts the inner diameter of the tip 250. This contact between the tip 250 and the balloon allows the physician to manipulate the position of the tip 250 within the delivery sheath. After the tip 250 is positioned within the intra-atrial septum 180 and the first anchor 262 deployed, the delivery sheath may be retracted from the surgical site. Alternatively, the delivery sheath may be constructed from a peel away material such that the delivery sheath is split and removed from the surgical site.

Referring still to FIGS. 9 and 9A, the proximal end portion 252 of the tip 250 may be shaped to receive and secure a second anchor 270 that includes a plurality of struts 272 coupled to a band 274. The struts 272 may be constructed to extend from a common ring structure 276 that is affixed within a groove 278 of the band 274. The struts 272 of the second anchor 270 may be operable to move from a contracted state (for insertion as described below) to an extended state and may be machined from a tubular structure formed using wire or formed from a flat sheet stock, as was described above. The wire or flat sheet stock may be any shape-memory material (such as nickel titanium, NiTi, or MP35N). While many shapes for the struts 272 are possible, the shape shown includes an angled portion 272a and a contact portion 272b when the strut 272 is in the extended state. The contact portion 272b will contact the biologic tissue while the angled portion 272a allows the anchor 270 to accommodate a wide range of anatomies and tissue thicknesses. The angled portion 272a also creates a force that will resist a distal movement of the anchor 170 after it has been properly attached to the tip 250.

The band 274 may be constructed from materials and using methods that are similar to the tip 250. As shown in FIG. 9A, the band 274 is shaped and sized to be received by the proximal end portion 252 of the tip 250, and secured by friction fit, interference fit, a magnet, a screw thread or other in vivo assembly methods that are generally known.

For delivery, the second anchor 270 is positioned onto a first delivery sheath 242 having notches 244 in which the plurality of struts 272 rest in a contracted state and in a proximal direction. The notches 244 contribute to the over-all low profile assembly for percutaneous delivery of the second anchor 270. The first delivery sheath 242 and the second anchor 270 are preloaded into a second delivery sheath 248 and, as a unit, are percutaneously directed to the previously inserted tip 250. With sufficient distally-directed force, the band 274 is attached to the proximal end portion 252 of the inserted tip 250 by a mechanical connection. The plurality of struts 272 are then deployed by retracting the second delivery sheath 248 from the intra-atrial septum 180, which may include pulling on one or more connector members 246 that extend proximally from the second delivery sheath 248 into the hub catheter insertion site (not shown). After sufficient retraction, the struts 272 deploy from the contracted state to the deployed state against the intra-atrial septum 180. Both of the first and second delivery sheaths 242, 248 may then be retracted away from the tip 250.

As is further shown in FIG. 9, the struts 264, 272 of one or both anchors 262, 270 may include a porous polymeric structure 280 to provide a larger surface for engaging the intra-atrial septum 180 (FIG. 9A) than the plurality of struts 264, 272 alone. The porous polymeric structure 280 may also allow for tissue in-growth, wherein biologic tissue from the intra-atrial septum 180 may grow and embed within the porous polymeric structure 280 to provide greater structural stability and sealing capacity. Suitable materials for the porous polymeric structure 280 may include, but are not limited to, polyester monofilament or multifilament yarn; ePTFE monofilament or multifilament yarn; or fluorinated polyolefin fibers or yarns, which can be woven, braided, knitted, or felted into a proper configuration. The porous polymeric structure 280 may further include various intrinsic configurations including weaves, braids, or knits having two or three-dimensional honeycombs, circular, flat, or tri-axial tubular structures. In other embodiments, the porous polymeric structure 280 may be constructed from an ePTFE piece in tubular, cylindrical, or sheet form. Generally, the porous polymeric structure 280 will be constructed by etching or laser cutting a shape from two sheets of a stock material (such as those described above). The shaped polymeric structures 280 are then ultrasonically welded together such that the shaped polymeric structures 280 capture the struts 264, 272 therebetween.

FIG. 9 further illustrates that the anchors 262, 270 may be positioned such that the struts 264 of the first anchor 262 are offset with respect to the struts 272 of the second anchor 270. This configuration has particular load-bearing benefits but should not be considered to be required.

Figure 10A:
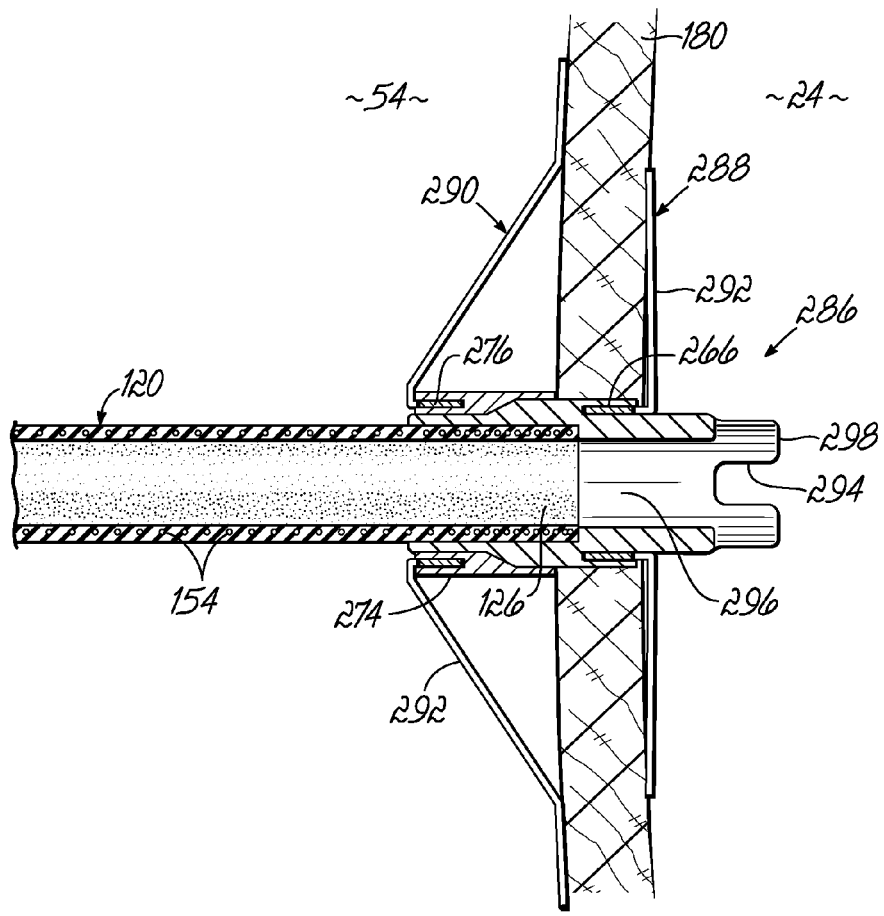
FIG. 10A is an enlarged cross-sectional view of the cannula tip of FIG. 10 implanted across the intra-atrial septum.

Turning now to FIGS. 10 and 10A were yet another illustrative embodiment of a tip 286 is shown. The tip 286 is constructed in a manner that is similar to the tip 182 (FIG. 4) but includes a first anchor 288 and an engagable second anchor 290 that are similar to those shown in FIG. 9 but without including the porous polymeric structure 280 (FIG. 9). The anchors 288, 290 each include a plurality of struts 292 for residing on opposing sides of the intra-atrial septum 180. The tip 286 further includes at least one opening 294, illustrated as a plurality of notches, extending proximally from a distal end 298 for providing fluidic access to the lumen 296 of the tip 286 should the distal tip end 298 become occluded or obstructed.

Figure 11:
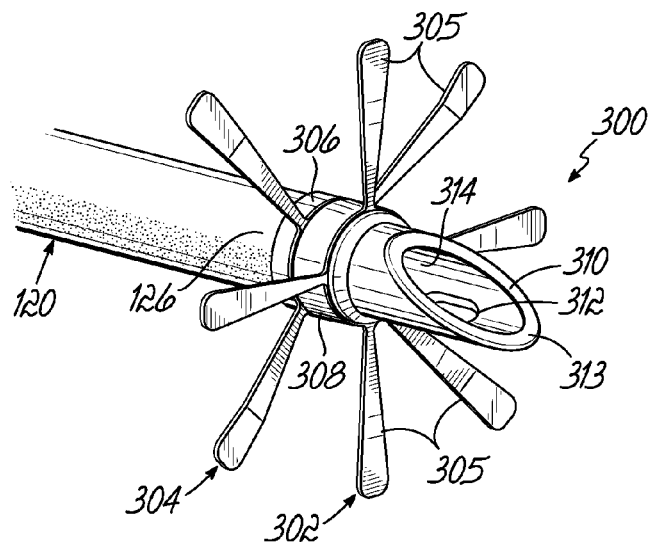
FIG. 11 is a perspective view of the inflow cannula including yet another transseptal embodiment of the cannula tip.
Figure 11A:
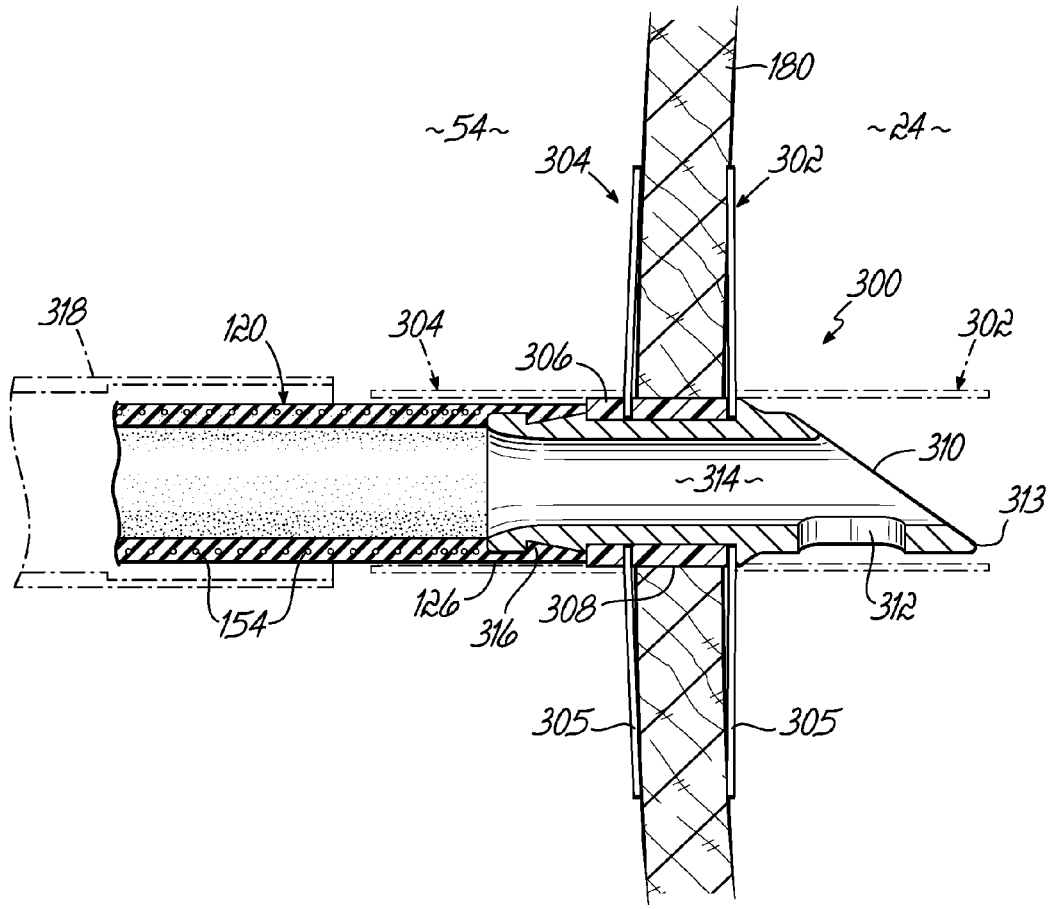
FIG. 11A is an enlarged cross-sectional view of the cannula tip of FIG. 11 implanted across the intra-atrial septum.

FIGS. 11 and 11A illustrate yet another embodiment of a one-piece intra-septal tip 300 having first and second anchors 302, 304 coupled thereto and each including a plurality of struts 305 that may be percutaneously delivered to the biologic tissue with a single delivery sheath 318. The tip 300 includes one or more rings 306 that are provided for several reasons. These rings 306 may act in a manner so as to engage the anchors 302, 304 and/or act in cooperation with one or more clamps 308 to affix the anchors 302, 304 on the tip 300. Suitable clamps 308 may include swage or crimp-style clamps or may be attached to the tip 300 by an adhesive, welding, or tying.

The tip 300, as shown, further includes a structure that is similar to the tip 196 of FIG. 5 having two openings 310, 312, e.g., the opening 310 defined by an inclined distal end surface that extends proximally from a distal tip end 313 of the tip 196 and the opening 312 defined by an opening in the form of an aperture. The openings 310, 312 reduce the likelihood of blockage or flow restriction into the lumen 314 when inserted through the intra-atrial septum 180. The tip 300 further includes barbs 316 for providing a frictional fit with the shaft 120.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combinations depending on the needs and preferences of the user. However, the invention itself should only be defined by the appended claims.

What is claimed is:

1. A cannula for insertion through a biologic tissue, the cannula comprising:
   a shaft comprising proximal and distal end portions and a lumen extending therebetween;
   a tip having a proximal end portion, a distal tip end, and a lumen extending therebetween, the proximal end portion of the tip being secured to the distal tip end of the shaft, and
   a hub having proximal and distal end portions and a lumen extending therebetween, the distal end portion of the hub positioned at the proximal end portion of the shaft such that the lumen of the hub is in fluid communication with the lumen of the shaft, and the proximal end portion of the hub is configured to be coupled to an auxiliary device,
   the tip having a first distal tip opening at the distal tip end and a second opening communicating with the lumen of the tip, the second opening extending proximally relative to the distal tip end, wherein the second opening of the tip extending proximally is configured to permit fluid to be continuously drawn into the lumen of the tip even in the event the distal tip opening becomes obstructed.

2. The cannula of claim 1, wherein the hub further comprises an inner cylindrical portion and a plurality of outer, longitudinally spaced annular members that are formed integral with the inner cylindrical portion, the longitudinally spaced annular members operable to control a kink radius of the hub.

3. The cannula of claim 1, wherein the shaft further comprises a composite construction comprising an inner liner, a reinforcing structure secured to the inner liner, and an outer jacket secured to the reinforcing structure and the inner liner.

4. The cannula of claim 3, wherein the inner liner comprises a co-extruded inner layer defining the lumen of the shaft and an outer layer bonded to the co-extruded inner layer.

5. The cannula of claim 4, wherein the co-extruded inner layer of the inner liner is made from a first thermoplastic material and the outer layer of the inner liner is made from a second thermoplastic material different from the first thermoplastic material.

6. The cannula of claim 3, wherein the outer jacket is bonded to the reinforcing structure and the inner liner.

7. The cannula of claim 3, wherein the reinforcing structure comprises a braided construction.

8. The cannula of claim 3, wherein the reinforcing structure is made from a metallic material or a polymeric material.

9. The cannula of claim 3, wherein the reinforcing structure comprises a coiled configuration.

10. The cannula of claim 1, wherein the second opening extending proximally includes at least one aperture extending between the lumen and an outer surface of the tip.

11. The cannula of claim 1, wherein the second opening extending proximally includes at least one notch extending proximally from the distal tip end and between the lumen and an outer surface of the tip.

12. The cannula of claim 1, wherein the second opening extending proximally includes a plurality of notches extending proximally from the distal tip end and between the lumen and an outer surface of the tip, the plurality of notches being spaced circumferentially around the tip.

13. The cannula of claim 1, wherein the second opening extending proximally includes an inclined edge extending proximally from the distal tip end, wherein the inclined edge is angled relative to a lengthwise central axis of the tip.

14. The cannula of claim 13, wherein the tip further includes a third opening extending proximally relative to the distal tip end, the third opening including at least one notch or at least one aperture.

15. The cannula of claim 1, wherein the tip further includes an outer surface having a frusto-conical shape that converges distally.

16. The cannula of claim 15, wherein the outer surface includes a shoulder configured to abut a first side of the biologic tissue when the tip is positioned through the biologic tissue.

17. The cannula of claim 16, wherein the shoulder is further configured to center the tip relative to the insertion position and to prevent tissue obstruction.

18. The cannula of claim 1, wherein the tip is constructed from a material that is molded such that the lumen is devoid of parting lines.

19. The cannula of claim 1, the tip is constructed from a metallic material.

20. The cannula of claim 19, wherein at least a portion of an outer surface of the tip promotes tissue in-growth.

21. The cannula of claim 1, wherein the tip further includes a first anchor that is configured to be deployed from a contracted state to an expanded state, wherein the first anchor is configured to engage at least one side of the biologic tissue in the expanded state and is operable to resist movement of the tip in at least one direction along a lengthwise central axis of the tip.

22. The cannula of claim 21, wherein the first anchor further comprises a plurality of struts extending generally transverse to the lengthwise central axis of the tip.

23. The cannula of claim 22, wherein the plurality of struts is formed from a superelastic material and are folded to a position generally parallel with the lengthwise central axis when in the contracted state and extend to a position generally transverse to the lengthwise central axis when in the expanded state.

24. The cannula of claim 22, wherein the first anchor further includes a porous polymeric structure coupled with the plurality of struts to facilitate tissue in-growth for securing the first anchor to the biologic tissue.

25. The cannula of claim 21 further comprising:
   a second anchor located proximal to the first anchor, the second anchor operable to prevent a movement of the tip in a distal direction.

26. The cannula of claim 25, wherein the second anchor further comprises a plurality of struts extending generally transverse to the lengthwise central axis of the tip.

27. The cannula of claim 26, wherein the plurality of struts is formed from a superelastic material and are folded to a position generally parallel with the lengthwise central axis when in the contracted state and extend to a position generally transverse to the lengthwise central axis when in the expanded state.

28. The cannula of claim 26, wherein the second anchor further includes a porous polymeric structure coupled with the plurality of struts and facilitating tissue in-growth for securing the second anchor to the biologic tissue.

29. A cannula for insertion through a biologic tissue, the cannula comprising:
a shaft comprising proximal and distal end portions and a lumen extending therebetween; and
a tip having a proximal end portion, a distal tip end, and a lumen extending therebetween, the proximal end portion of the tip being secured to the distal tip end of the shaft,
the tip having a first distal tip opening and a second opening communicating with the lumen of the tip, the second opening extending proximally relative to the distal tip end, wherein the second opening of the tip extending proximally is configured to permit fluid to be continuously drawn into the lumen of the tip even in the event the distal tip opening becomes obstructed,
wherein the tip is constructed from a thermoplastic material or a thermoset material and an inner surface of the tip includes an anti-thrombotic coating.

30. The cannula of claim 29, wherein an outer surface of the tip further includes a polymeric coating.

31. The cannula of claim 29, wherein an outer surface of the proximal end portion of the tip includes a coating that promotes thrombus formation.

32. A delivery system comprising:
a shaft comprising proximal and distal end portions and a lumen extending therebetween; and
a tip having a proximal end portion, a distal tip end, and a lumen extending therebetween, the proximal end portion of the tip being secured to the distal tip end of the shaft,
the tip having a first distal tip opening at the distal tip end and a second opening communicating with the lumen of the tip, the second opening extending proximally relative to the distal tip end, wherein the second opening of the tip extending proximally is configured to permit fluid to be continuously drawn into the lumen of the tip even in the event the distal tip opening becomes obstructed,
wherein the tip further includes a first anchor that is configured to be deployed from a contracted state to an expanded state, wherein the first anchor is configured to engage at least one side of the biologic tissue in the expanded state and is operable to resist movement of the tip in at least one direction along a lengthwise central axis of the tip, and
a delivery sheath configured to receive the cannula and to move relative thereto for deploying the first anchor into the expanded state.

33. The delivery system of claim 32, wherein the delivery sheath is constructed from a peel-away material.

* * * * *